United States Patent [19]
Dieken et al.

[11] Patent Number: 5,367,575
[45] Date of Patent: Nov. 22, 1994

[54] ELECTRONIC STETHOSCOPE HAVING BATTERY CARRIAGE

[75] Inventors: Alan P. Dieken; Gerald E. Drake, both of Oakdale, Minn.

[73] Assignee: Minnesota Mining and Manufacturing Company, St. Paul, Minn.

[21] Appl. No.: 992,850

[22] Filed: Dec. 16, 1992

[51] Int. Cl.$^5$ .............................................. A61B 7/04
[52] U.S. Cl. ....................... 381/67; 429/96; 429/100
[58] Field of Search ................ 429/96, 97, 98, 99, 429/100; 381/67, 69.2

[56] References Cited

U.S. PATENT DOCUMENTS

| | | | |
|---|---|---|---|
| 2,668,197 | 2/1954 | Gustafson et al. | 381/69.2 |
| 2,764,640 | 9/1956 | Osserman et al. | 381/69.2 |
| 3,301,712 | 1/1967 | Bach | 429/100 |
| 3,790,712 | 2/1974 | Andries . | |
| 4,071,694 | 1/1978 | Pfeiffer . | |
| 4,075,561 | 2/1978 | Stevens | 324/149 |
| 4,170,717 | 10/1979 | Walshe . | |
| 4,254,302 | 3/1981 | Walshe . | |
| 4,391,883 | 7/1983 | Williamson et al. | 429/97 |
| 4,429,025 | 1/1984 | Stow | 429/97 |
| 4,440,258 | 3/1984 | Packard | 181/137 |
| 4,578,628 | 3/1986 | Siwiak | 320/2 |
| 4,723,555 | 2/1988 | Shue | 128/715 |
| 4,878,501 | 11/1989 | Shue | 128/715 |
| 5,229,220 | 7/1993 | Stanton et al. | 429/100 |

FOREIGN PATENT DOCUMENTS 2659007 12/1989 France .

*Primary Examiner*—Forester W. Isen
*Attorney, Agent, or Firm*—Gary L. Griswold; Walter N. Kirn; William D. Bauer

[57] ABSTRACT

An electronic stethoscope which is adapted to receive auscultatory sounds from a body, is adapted to transmit the auscultatory sounds to a user, or other medical device which is adapted to be powered by a battery. The stethoscope has a chestpiece adapted to utilized in cooperation with the body, an acoustical transducer cooperating with the chestpiece for receiving the auscultatory sounds and transforming the auscultatory sounds into an electrical input signal. The stethoscope or medical device has an electronic processor for processing the electrical signal. The stethoscope has a speaker for converting the electrical output signal into an acoustical output signal and an earpiece receiving the acoustical output signal and providing the acoustical output signal to the user. The chestpiece (or housing of the medical device) has a cavity adapted to contain the battery. A battery carriage is insertable into the cavity of the chestpiece and is adapted to receive the battery before the battery carriage is inserted into the cavity of the chestpiece or housing. The battery carriage provides electrical continuity from the positive terminal of the battery to power supply circuitry when the battery carriage is inserted into the cavity of the chestpiece or housing. The battery carriage receives the battery in only one orientation with the positive terminal of the battery coupled to the positive electrical connection.

9 Claims, 3 Drawing Sheets

ELECTRONIC STETHOSCOPE HAVING BATTERY CARRIAGE

TECHNICAL FIELD

The present invention relates generally to electronic stethoscopes, and other battery powered medical devices, and, more particularly, to electronic stethoscopes, and other battery powered medical devices, having provision for installing, holding, connecting and removing batteries.

BACKGROUND OF THE INVENTION

Stethoscopes have long been used by physicians to monitor auscultatory sounds. Typically stethoscopes have been comprised of a head or chestpiece, a sound transmission mechanism and an earpiece assembly. The chestpiece is adapted to be placed near or against the skin, body, of a patient for gathering the auscultatory sounds. The sound transmission mechanism transmits the gathered sound to an earpiece, or a pair of earpieces, where the physician may monitor the sound.

The chestpiece of conventional acoustic stethoscopes are usually quite simple physically. They are usually round disk shapes sometimes dual sided, top and bottom, to allow either side of the chestpiece to contact the skin of the patient, perhaps for the gathering of auscultatory sounds in different frequency ranges.

Recently, some stethoscopes have utilized electronics for at least part of the sound processing path. In most of these devices, the auditory sound is picked up by a microphone usually located in a detection device which is similar to the chestpiece of a conventional auditory stethoscope in external appearance. The electrical signal from the microphone is then processed electronically and is coupled to a speaker, or speakers, where the electrical signal is converted back into an auditory sound for reception by the physician. Of course, other electronic analysis or display of the auscultatory sounds may be performed by the signal processor, either in addition to or instead of the usual conversion back into an auditory sound.

The incorporation of electronic circuitry into the stethoscope has been a considerable design problem for the engineer. Typically, the electronic circuitry increases the physical size of the stethoscope package. Either the size of the chestpiece is increased in size dramatically or an additional enclosure to house the electronics is located between the chestpiece and earpiece assembly or both. In both of these cases, the resulting stethoscope is bulky, cumbersome to use and not easily storable between uses.

Since, stethoscopes are by necessity portable devices and since the electrical components of electronic stethoscopes require a source of electrical power, electronic stethoscopes must be battery powered. Also, since the physician has become accustomed to handling and using a conventional acoustic stethoscope, an electronic stethoscope must by physically sized and configured to resemble its conventional acoustic predecessor. Further constraints placed upon the electronic stethoscope include the demands of reliability, long battery life, light weight, isolation from external sounds, maintenance of high signal quality.

U.S. Pat. No. 4,170,717, Walshe, Electronic Stethoscope; U.S. Pat. No. 3,790,712, Andries, Electronic Stethoscope System; U.S. Pat. No. 4,878,501, Shue, Electronic Stethoscope Apparatus; and French Patent Publication No. 2,659,007, Oclin, Stethoscope With Electronic Amplification, generally describe electronic stethoscopes.

U.S. Pat. No. 4,071,694, Pfeiffer, Stethoscope, (assigned to the assignee of the present invention) describes a stethoscope which has both an electronic and an acoustic capability. The chestpiece of the stethoscope described in the Pfeiffer patent has a conventional shape and achieves a conventional function. The chestpiece is round and generally flat making the stethoscope appear and handle similarly to conventional stethoscopes. The stethoscope contains a battery holder (37) formed of an insulating material such as polypropylene placed on top of a printed circuit board (34) clamping the printed circuit board to the housing. In addition to having a pair of cavities (38) for flat, round batteries (39), the battery holder also serves as a cover for the volume control (35) and frequency selector (36). The battery holder is also provided with a cylindrical guide sleeve (40) for push button on-off switch (41)

U.S. Pat. No. 4,254,302, Walshe, Electronic Stethoscope, illustrates a circular holder (194) for two replaceable batteries (190 & 191) contained in wells (192 & 193). The holder is received in body bore (196) against shoulder (197). A metallic terminal strip (198) on disc (199) engages the battery terminals (190a & 191a) when cap (160) is in place. Different sized studs (200 & 201) on the disc (199) interfit locator stud holes (203 & 204) in the holder (194).

Other patents describe various battery powered electronic apparatus but which fail to provide the significant advantages of the present invention.

For example, U.S. Pat. No. 4,075,561, Stevens, Programmable Electrical Apparatus Containing a Battery, describes an electrical apparatus, watt-hour meter, enclosed within a housing which contains a replaceable battery. A composite unit (16) provides the dual functions of battery support and terminal connector and cooperates with an access port or service entry (14) in the housing (12). The composite unit includes an integral structure containing support or receptacle for a battery, such as dry cell battery (18), which may comprise a hollow cylinder or tubular body providing a receptacle or chamber (20) for the retainment of a battery in its designated position within the apparatus and in electrical contact with the terminals therefor. Battery chamber (20) is provided with a plurality of longitudinal spacing ribs (22) for the support of the battery. The composite unit provides connecting terminal (26) for terminal post (24) of the battery and connecting terminal (30) for terminal post (28) of the battery.

Also U.S. Pat. No. 4,391,883, Williamson et al, Housing Arrangement With Breakaway Battery Access Door, describes a battery powered device (10) having a battery compartment with an integral battery door assembly (12). The battery door is hinged permitting outward pivoting from the housing. A latch mechanism (20) may be operated to latch and unlatch the door. The battery door assembly (12) includes two horizontal wing members (28) which cylindrically hold the cylindrical battery (18). When battery (18) is positioned within cavity (16), respective ends thereof are placed in contact with terminals (40) which supply power to the electrical circuitry.

U.S. Pat. No. 4,578,628, Siwiak, Portable Battery Powered Electrical Apparatus With Improved Battery Pack Protected Against Inadvertent Short Circuit of the Battery Terminals, discloses a portable radio transceiver (10) having a removable battery pack (14). The battery pack includes a battery power source (15). The battery (15) makes electrical contact within the battery pack (14) and is coupled to terminals (18) on the battery pack through a normally open switch (20). Switch (20) is not closed until the battery pack is coupled to the transceiver, thus preventing any accidental short circuiting of the battery.

U.S. Pat. No. 4,429,025, Stow, Battery Retaining Device, discloses a retaining device suitable for removably interconnecting a battery with the housing of an electrical apparatus. The retaining device has a bracket provided with two stanchions adapted to receive the battery in a battery retention channel.

SUMMARY OF THE INVENTION

The presently claimed invention provides an electronic stethoscope which is electrically powered by a long-life battery, is small, is light weight, provides for easy replacement of the battery, is vibration proof, shock proof and dust resistant, prevents damage to internal circuitry with reverse orientation of the battery and enables the stethoscope to have clarity of sound by ensuring isolation from noisy surroundings.

The present invention provides an electronic stethoscope which is adapted to receive auscultatory sounds from a body, is adapted to transmit the auscultatory sounds to a user, and is adapted to be powered by a battery. The stethoscope has a chestpiece adapted to be utilized in cooperation with the body, an acoustical transducer cooperating with the chestpiece for receiving the auscultatory sounds and transforming the auscultatory sounds into an electrical input signal, a signal processor for processing the electrical input signal to produce an electrical output signal, a speaker for converting the electrical output signal into an acoustical output signal and an earpiece receiving the acoustical output signal and providing the acoustical output signal to the user. The chestpiece has a cavity adapted to contain the battery. A battery carriage is insertable into the cavity of the chestpiece and is adapted to receive the battery before the battery carriage is inserted into the cavity of the chestpiece. The battery carriage provides electrical continuity from the positive terminal of the battery to power supply circuitry when the battery carriage is inserted into the cavity of the chestpiece. The battery carriage receives the battery in either orientation, but will allow electrical connection in only the one orientation wherein the positive terminal of the battery coupled to the positive electrical connection of the power supply circuitry.

In an alternative embodiment, the present invention provides a battery powered medical device providing a medical function. The device has electrical means for performing at least a portion of the medical function of the medical device, a housing having a cavity adapted to contain a battery type of energy source and power supply circuitry for supplying electrical power from the battery to the electrical means, the power supply circuitry having a positive electrical connection and a negative electrical connection. A battery carriage is insertable into the cavity of the housing and is adapted to receive the battery before the battery carriage is inserted into the cavity of the housing. The battery carriage provides electrical continuity from the positive terminal of the battery to the power supply circuitry when the battery carriage is inserted into the cavity of the housing. The battery carriage receives and makes contact with one or more batteries in only one orientation with the positive terminal of the battery being coupled to the positive electrical connection.

Preferably, the battery carriage receives the battery so that the positive terminal of the battery can only be electrically coupled to the positive electrical connection of the power supply circuitry. Also preferably, the battery carriage slides into the cavity of the chestpiece or housing. Preferably, the battery carriage provides a wiping or cleaning action for the positive electrical connection upon the insertion of the battery carriage into the chestpiece or housing.

In a preferred embodiment, the chestpiece or housing further has an electrical connection to the negative terminal of the battery and the battery carriage provides for direct electrical connection between the negative terminal of the battery and the electrical connection to the negative terminal of the power supply circuitry.

In a preferred embodiment, the battery carriage has a plurality of spring loaded guide rails, the guide rails providing a guideway spacing the battery away from the signal processor and positively and securely holding the battery within the carriage and securing holding the carriage with respect to the chestpiece or housing.

In a preferred embodiment, the battery carriage further has a cover providing dust and splash resistance to the cavity of the chestpiece or housing when the battery carriage is inserted into the cavity and a latch cooperating with the cover and the chestpiece or housing and positively securing the carriage to the chestpiece or housing.

In a preferred embodiment, the chestpiece or housing has a generally planar surface adapted to be placed adjacent the body, wherein the chestpiece or housing has a surface opposite the generally planar surface generally forming an oblique angle therewith, wherein the chestpiece or housing has side walls generally enclosing the chestpiece or housing, one of the side walls having an opening adapted to receive the battery carriage, the cover of the battery carriage covering the opening.

Preferably, the longitudinal axis of the battery coincides with the longitudinal axis of the battery carriage, the longitudinal axis of the battery generally being parallel with the surface opposite the generally planer surface of the chestpiece or housing.

In a preferred embodiment, the electronic stethoscope also has a tubular member coupling the chestpiece or housing to the earpiece, the tubular member mating with the chestpiece or housing along one of the side walls, the longitudinal axis of the battery forming an oblique angle with respect to a longitudinal axis of the tubular member.

BRIEF DESCRIPTION OF THE DRAWINGS

The foregoing advantages, construction and operation of the present invention will become more readily apparent from the following description and accompanying drawings in which.

DETAILED DESCRIPTION OF THE PREFERRED EMBODIMENTS

Electronic medical devices often must be made small and portable, Examples include stethoscopes and other electronic prostheses such as hearing aids and transcutaneous electrical nerve stimulators. While this list is not exclusive, it generally indicates the problems which are associated with designing and producing small, portable electronic medical devices. Requirements for such devices are typically light weight and ease of battery replacement. These requirements are especially true of electronic stethoscopes in which the electronic version must be made similar to the weight, feel and ease of use of their conventional acoustic counterparts. An electronic stethoscope must also be extremely reliable. It must be available for use at the beck and call of the physician. In order to promote reliability, the electronic stethoscope should have resistance to dust and other contaminants and resistance to vibration and shock such as from accidental dropping or banging by the physician.

In addition, electronic stethoscopes must offer sound isolation from the surroundings in which the stethoscopes is used. In order for the physician to gain the most advantageous use of the stethoscope, the stethoscope should provide the highest possible clarity of auscultatory sound from the patient, body, as well as provide the greatest possible isolation from all extraneous sounds from the surrounding environment.

Stethoscopes have long been used by physicians to monitor auscultatory sounds. Typically stethoscopes have been comprised of a head or chestpiece, a sound transmission mechanism and an earpiece assembly. The chestpiece is adapted to be placed against the skin of a patient for gathering the auscultatory sounds. The sound transmission mechanism transmits the gathered sound to the earpiece where the physician may monitor the sound.

Figure 1:
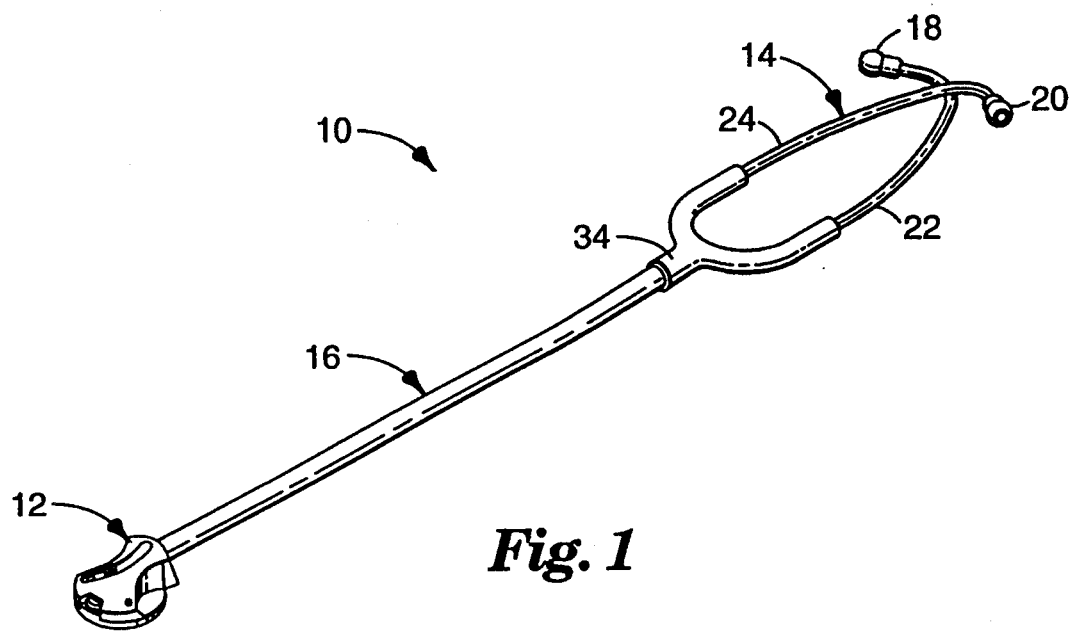
FIG. 1 is a perspective view of a stethoscope utilizing the present invention.

The stethoscope 10 illustrated in FIG. 1 consists of a chestpiece 12, or stethoscope head, a binaural assembly 14 and a connecting tube 16. The binaural assembly 14 has two earpieces 18 and 20 adapted to fit in or near the ear of a user, typically a physician or other medical professional. Tubes 22 and 24, generally acoustic tubes, couple earpieces 18 and 20, respectively, to connecting tube 16 which in turn is coupled to chestpiece 12.

Figure 2:
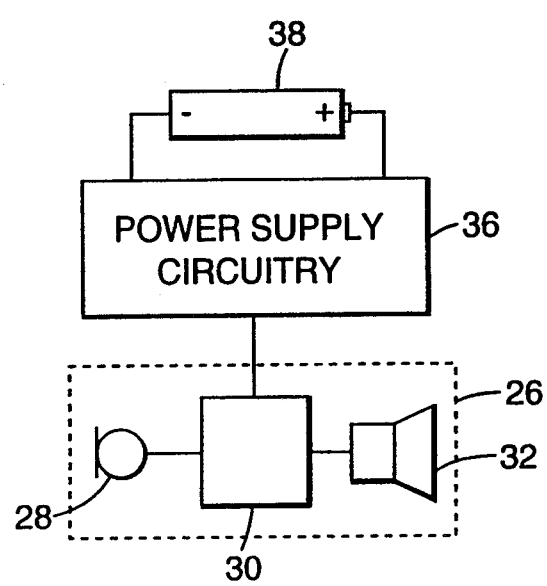
FIG. 2 is a functional block diagram of a stethoscope utilizing the present invention.

The sound transmission system of stethoscope 10 may be entirely electronic or may be a combination acoustic and electronic, or dual acoustic and electronic. A simplified block diagram of the electronic transmission system 26 is illustrated in FIG. 2. An acoustic to electronic transducer, a microphone, 28 would be located along the acoustic sound transmission path, typically in or very near the chestpiece 12, and even more typically positioned near the bottom surface of the chestpiece 12 so as to be near the source of auscultatory sounds. A signal processor 30 amplifies, or otherwise processes, the electrical signal. An electrical to acoustic transducer, a speaker, 32 is preferably located near juncture 34 of connecting tube 16 and earpiece tubes 22 and 24 of the stethoscope 10 illustrated in FIG. 1. Speaker 32 transforms the auscultatory sounds back to the acoustic domain where tubes 22 and 24 transmit the acoustic sounds to earpieces 18 and 20, respectively. Other locations for speaker 32 are also contemplated such as within, or closer to, chestpiece 12 or perhaps separate speakers located near earpieces 18 and 20. Although it is preferred that stethoscope 10 have a binaural earpiece assembly, other forms of reception of the auscultatory sounds are envisioned such as a monaural earpiece, a single headset, or other sound recording or receiving mechanism.

The electronic transmission system 26 of stethoscope 10 is powered through power supply circuitry 36 which in turn receives electrical power from battery, or a series of batteries, 38. Typically, microphone 28, signal processor 30, power supply circuitry 36 and battery 38 are all located within chestpiece 12.

For ease of battery replacement, protection of electronic circuit components, and to prevent accidental connection in reverse battery polarity, battery 38 is not inserted directly into chestpiece 12. Rather battery 38 is first inserted into a holder, or battery carriage 40, which in turn is inserted into chestpiece 12 of stethoscope 10.

Figure 3:
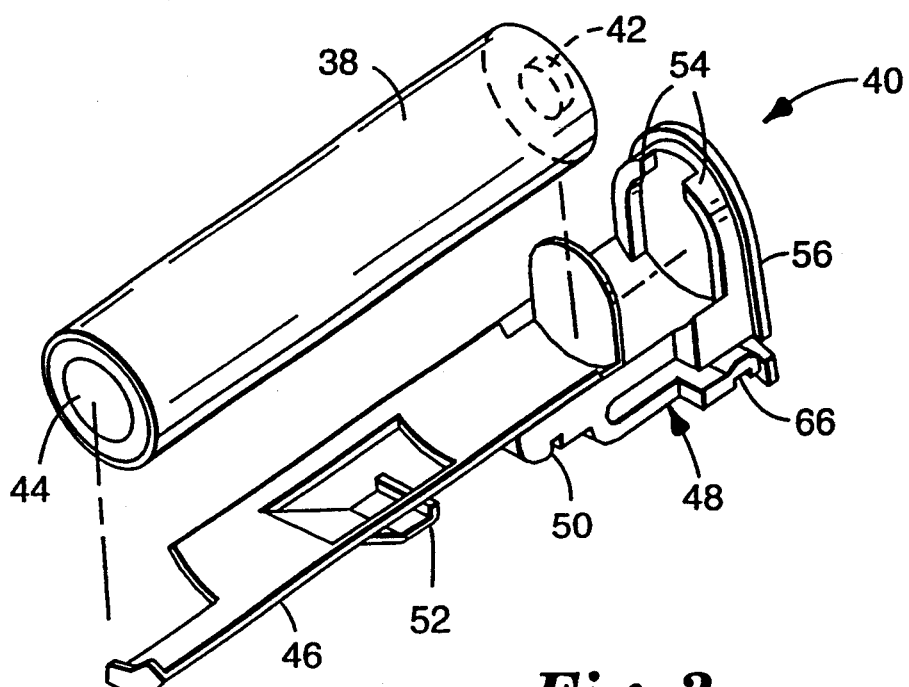
FIG. 3 is a exploded perspective view of a battery carriage, including the battery, utilizable in the present invention.

Battery carriage 40 is illustrated separately from chestpiece 12 in FIG. 3. Battery 38 is preferably a common size AAA alkaline battery. Battery 38 has a positive terminal 42 and a negative terminal 44. As is conventional, positive terminal 42 protrudes from the end of battery 38 and negative terminal 44 is flush with the opposite end of battery 38. Battery carriage 40 is preferably formed of battery holder 46 which is shaped to allow the battery 38 to be snapped into place. Battery holder 46 preferably is made of an electrically conductive material such as 316 series stainless steel. Battery holder 46 is attached to door assembly 48 in recess 50 which mates with flange 52 of battery holder 46 and by shoulders 54. Door assembly 48 is preferably made from an electrically non-conductive material such as polycarbonate, No. 1120 or 1121 available from the General Electric Company.

Constructed in this manner, battery carriage 40 provides an electrical connection from positive terminal 42 of battery 38 to power supply circuitry 36 contained in chestpiece 12 when battery carriage 40 is inserted into chestpiece 12. Negative terminal 44 is directly available to an electrical contact within chestpiece 12 when battery carriage 40 is inserted properly.

Shoulders 54 allow positive terminal 42 of battery 38 to contact the electrically conductive battery holder 46 but will not allow negative terminal 44 of battery 38 to contact electrically conductive battery holder 46, thus eliminating possible damage to the electronic circuitry (signal processor 30) due to accidental insertion and connection of battery 38 backward or possible incorrect choice of battery 38. Further, if battery 38 were reversed in battery carriage 40, shoulders 54 would prevent battery 38 from being flush with door 56. This would make the combined battery carriage 40 and battery 38 longer with battery 38 reversed than would be the case if battery 38 were properly installed. The longer dimension may be used in conjunction with mating components in chestpiece to prevent battery carriage 40 from being fully inserted and seated into chestpiece, thus properly pointing out the user the incorrect polarity of battery 38.

Door 56 of battery carriage 40 closes the opening in chestpiece 12 which allows insertion when battery carriage 40 is fully inserted. This closure not only provides a clean, aesthetic look but also provides substantial functional benefits as well. Door 56 seals out contaminants from possibly entering chestpiece and contributes to isolating the electrical and acoustic components of stethoscope 10 from external noises.

Figure 4:
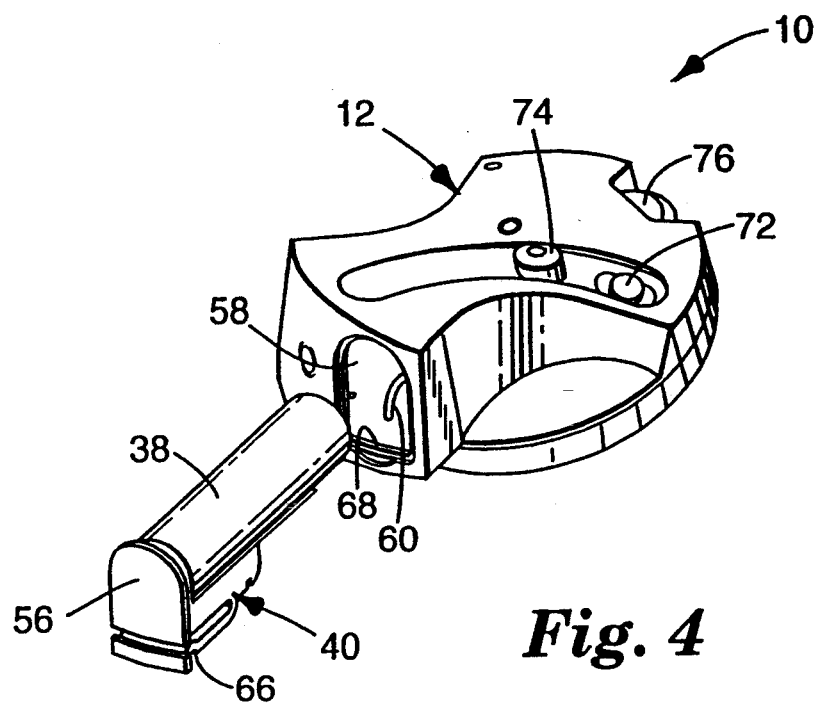
FIG. 4 is a perspective view of a stethoscope chestpiece with the battery carriage of FIG. 3 withdrawn.
Figure 5:
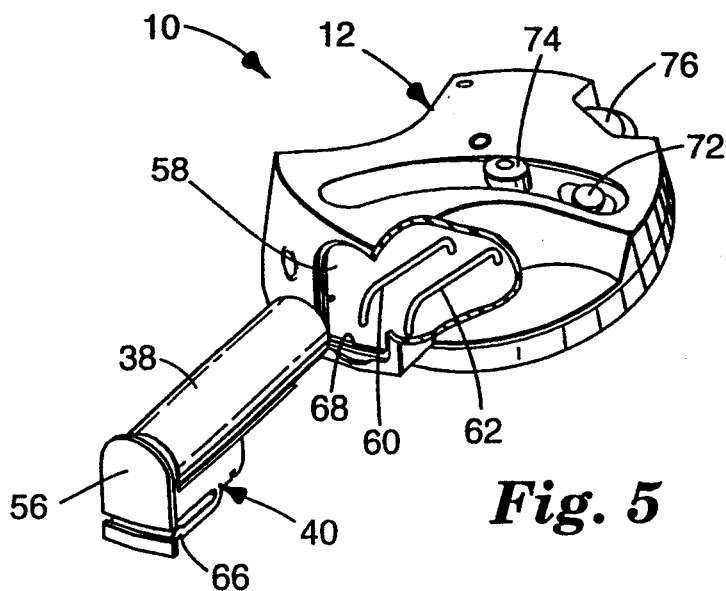
FIG. 5 is a partially cut away view of a stethoscope chestpiece as in FIG. 4.
Figure 6:
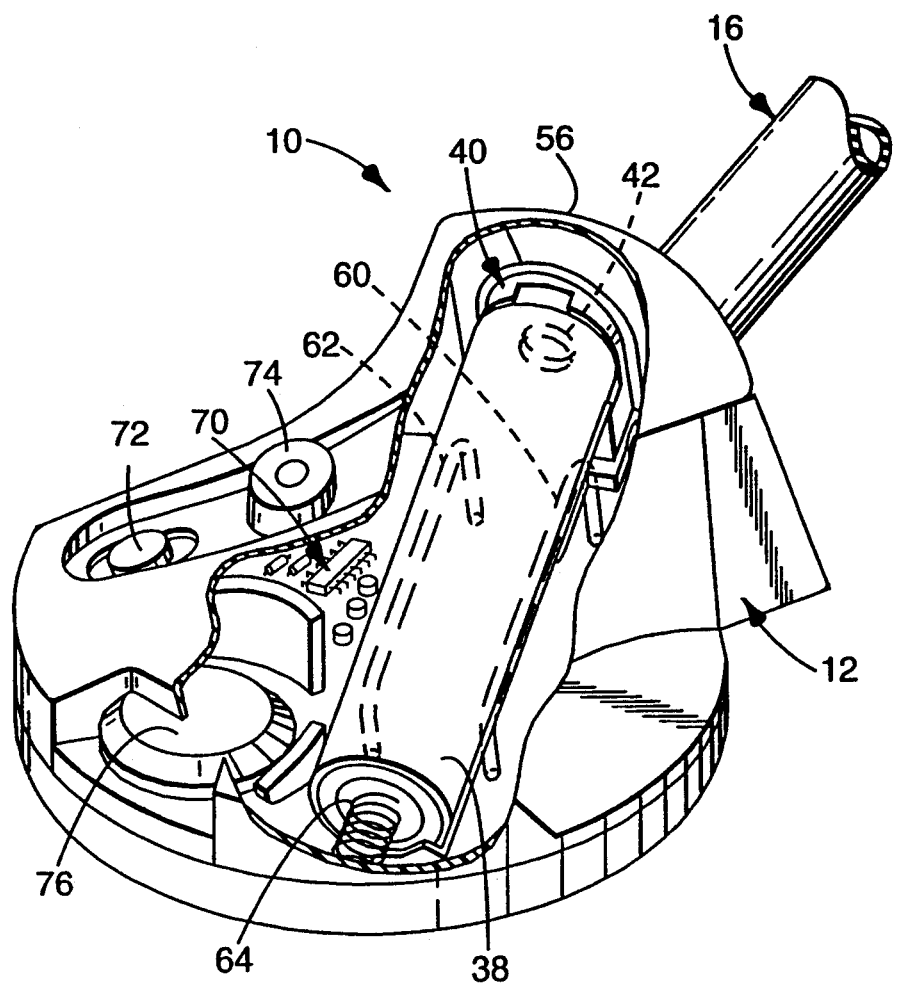
FIG. 6 is a partially cut away perspective view of a stethoscope chestpiece utilizing the present invention.

As can be seen in FIGS. 4, 5 and 6, battery carriage 40 with battery 38 can be inserted by sliding action into chestpiece 12 of stethoscope 10. Battery carriage 40 is inserted through opening 58 in chestpiece 12. Battery carriage is inserted at a diagonal across and down the interior of chestpiece 12 thus avoiding possible control elements on the top surface of chestpiece. Battery carriage 40 is held in position by spring action from spring loaded guide rails 60 and 62 which protect the electronic circuitry 70 of chestpiece 12 during insertion and removal of battery carriage 40. Guide rails 60 and 62 also provide electrical contact to one terminal, e.g., positive terminal 42, of battery 38 from battery holder 46. Electrical contact to the second terminal, e.g., negative terminal 44, of battery 38 is through stationary spring contact 64 contained within chestpiece 12.

The battery carriage is inserted through the rear wall of chestpiece 12 through opening 58 and guided into position by guide rails 60 and 62. Door 58 forms a closure in chestpiece 12, is held in place with latch 66. Chestpiece 12 is than made splash proof and dust proof by mating of door 56 with the body flange 68. The splash proof and dust proof closure thus protects the internal components from damage from water and/or other liquid and solid particles as may come in contact with stethoscope 10 in normal usage. Preferred material for the chestpiece 12 housing is polycarbonate. Other possible materials would include stainless steel, aluminum and various moldable plastic compounds.

Guide rails 60 and 62, illustrated in FIGS. 5 and 6, show the position with respect to electronic circuitry 70 and the bowed shape that is deflected during insertion of battery carriage 40 with battery 38 forcing contact with the housing of chestpiece 12, thus restraining battery 38 from moving within chestpiece 12 during use. Wiping action occurs during each insertion cleaning the electrical contact surfaces of guide rails 60 and 62 thus, eliminating circuit noise caused by power source contact impedance. Such positive securing of battery carriage 40 within chestpiece 12 also prevents vibration and maintains proper electrical contact during usage.

The angled direction of insertion of battery carriage 40 into chestpiece 12 provides several advantages. Battery carriage 40 is angled as viewed from a top view in order to fit into the raised ergonometric portion of chestpiece. Such angling also allows for the maximum amount of electronic real estate to remain inside chestpiece 12 after battery carriage 40 is inserted. Such angling also allows connecting tube 16 to be positioned in or close to its normally expected exact center rear position. Battery carriage 40 is also angled as viewed from a side view of chestpiece 12. This allow battery carriage 40 to follow the ergonometric shape of the sloped top surface of chestpiece 12. It also allows for the maximum amount of electronic real estate to remain.

One or more operational controls 72 and 74 may be positioned on the top surface of chestpiece 12. Typical uses of operational controls 72 and 74 are to turn power to the stethoscope 10 on, or off, or to change modes of operation. A rotary control 76 may also be located on chestpiece 12 and may be used to increase or decrease the volume of the auscultatory sound delivered to the user or control other functions as appropriate.

Thus, it can be seen that there has been shown and described a novel electronic stethoscope having a battery carriage. It is to be recognized and understood, however, that various changes, modifications and substitutions in the form and the details of the present invention may be made by those skilled in the art without departing from the scope of the invention as defined by the following claims.

What is claimed is:

1. An electronic stethoscope adapted to receive auscultatory sounds from a body, adapted to transmit, said auscultatory sounds to a user, and adapted to be powered by a battery having a positive terminal and a negative terminal, comprising:

a chestpiece adapted to be utilized in cooperation with said body;

an acoustical transducer cooperating with said chestpiece for receiving said auscultatory sounds and transforming said auscultatory sounds into an electrical input signal;

signal processing means being operatively coupled to said acoustical transducer for processing said electrical input signal to produce an electrical output signal;

speaker means operatively coupled to said signal processing means for converting said electrical output signal into an acoustical output signal;

an earpiece receiving said acoustical output signal and providing said acoustical output signal to, said user;

said chestpiece having a cavity adapted to contain said battery;

power supply means for supplying electrical power from said battery to said signal processing means, said power supply means having a positive electrical connection and a negative electrical electrical connection; and a battery carriage being slidably insertable into said cavity of said chestpiece and adapted to receive said battery before said battery carriage is inserted into said cavity of said chestpiece, said battery carriage providing electrical continuity from said battery to said power supply means when said battery carriage is inserted into said cavity of said chestpiece, said battery carriage receiving said battery in only one orientation with said positive terminal of said battery being electrically coupled to said positive electrical connection;

said battery carriage receiving said battery so that said positive terminal of said battery can only be electrically coupled to said positive electrical connection of said power supply means;

wherein said battery carriage provides a wiping action for said positive electrical connection upon said insertion of said battery carriage into said chestpiece.

2. An electronic stethoscope as in claim 1 wherein said chestpiece further comprises an electrical connection to said negative terminal of said battery and wherein said battery carriage provides for alignment of said electrical connection coupling between said negative terminal of said battery and said electrical connection in said chestpiece.

3. An electronic stethoscope adapted to receive auscultatory sounds from a body, adapted to transmit said auscultatory sounds to a user, and adapted to be powered by a battery having a positive terminal and a negative terminal, comprising:

a chestpiece adapted to be utilized in cooperation with said body;

an acoustical transducer cooperating with said chestpiece for receiving said auscultatory sounds and transforming said auscultatory sounds into an electrical input signal;

signal processing means being operatively coupled to said acoustical transducer for processing said electrical input signal to produce an electrical output signal;

speaker means operatively coupled to said signal processing means for converting said electrical output signal into an acoustical output signal;

an earpiece receiving said acoustical output signal and providing said acoustical output signal to said user;

said chestpiece having a cavity adapted to contain said battery;

power supply means for supplying electrical power from said battery to said signal processing means, said power supply means having a positive electrical connection and a negative electrical connection; and a battery carriage being insertable into said cavity of said chestpiece and adapted to receive said battery before said battery carriage is inserted into said cavity of said chestpiece, said battery carriage providing electrical continuity from said battery to said power supply means when said battery carriage is inserted into said cavity of said chestpiece, said battery carriage receiving said battery in only one orientation with said positive terminal of said battery being electrically coupled to said positive electrical connection;

wherein said chestpiece has a plurality of spring loaded guide rails, said guide rails providing a guideway spacing said battery away from said signal processor and positively and securely holding said battery within said carriage and securely holding said carriage with respect to said chestpiece.

4. An electronic stethoscope as in claim 3 wherein said battery carriage further comprises:

a cover providing dust and splash resistance to said cavity of said chestpiece when said battery carriage is inserted into said cavity; and a latch cooperating with said cover and said chestpiece and positively securing said carriage to said chestpiece.

5. An electronic stethoscope as in claim 4 wherein said chestpiece has a generally planar surface adapted to be placed adjacent said body, wherein said chestpiece has a surface opposite said generally planar surface generally forming an oblique angle therewith, wherein said chestpiece has side walls generally enclosing said chestpiece, one of said side walls having an opening adapted to receive said battery carriage, said cover of said battery carriage covering said opening.

6. An electronic stethoscope as in claim 5 wherein a longitudinal axis of said battery coincides with a longitudinal axis of said battery carriage, said longitudinal axis of said battery generally being parallel with said surface opposite said generally planer surface of said chestpiece.

7. An electronic stethoscope as in claim 6 further comprising a tubular member coupling said chestpiece to said earpiece, said tubular member mating with said chestpiece along one of said side walls, said longitudinal axis of said battery forming an oblique angle with respect to a longitudinal axis of said tubular member.

8. A battery powered medical device providing a medical function, said battery having a positive terminal and a negative terminal, comprising:

electrical means for performing at least a portion of said medical function of said medical device;

a housing having a cavity adapted to contain said battery;

power supply means for supplying electrical power from said battery to said electrical means, said power supply means having a positive electrical connection and a negative electrical connection; and a battery carriage being insertable into said cavity of said housing and adapted to receive said battery before said battery carriage is inserted into said cavity of said housing, said battery carriage providing electrical continuity from said battery to said power supply means when said battery carriage is inserted into said cavity of said housing, said battery carriage receiving said battery in only orientation with said positive terminal of said battery coupled to said positive electrical connection;

wherein said housing has a plurality of spring loaded guide rails, said guide rails providing a guideway spacing said battery away from said electrical means and positively and securely holding said battery within said carriage and securely holding said carriage with respect to said housing.

9. A medical device as in claim 8 wherein said battery carriage further comprises:

a cover providing dust and splash resistance to said cavity of said housing when said battery carriage is inserted into said cavity; and a latch cooperating with said cover and said housing and positively securing said carriage to said housing.

* * * * *

UNITED STATES PATENT AND TRADEMARK OFFICE
CERTIFICATE OF CORRECTION

PATENT NO. : 5,367,575
DATED : November 22, 1994
INVENTOR(S) : Dieken et al.

It is certified that error appears in the above-indentified patent and that said Letters Patent is hereby corrected as shown below:

Column 8, line 9, delete "transmit, said" and insert --transmit said--.

Column 8, line 34, delete the second occurrence of "electrical".

Column 10, line 36, after the word "only", and before the word "orientation", insert --one--.

Signed and Sealed this

Twenty-first Day of February, 1995

Attest:

BRUCE LEHMAN

*Attesting Officer*     *Commissioner of Patents and Trademarks*